(12) United States Patent
Nygaard (10) Patent No.: US 8,460,863 B2
(45) Date of Patent: Jun. 11, 2013

(54) DRY STICK DEVICE AND METHOD FOR DETERMINING AN ANALYTE IN A SAMPLE

(75) Inventor: Lars Nygaard, Græsted (DK)

(73) Assignee: Lattec I/S, Hillerod (DK)

(*) Notice: Subject to any disclaimer, the term of this patent is extended or adjusted under 35 U.S.C. 154(b) by 0 days.

(21) Appl. No.: 13/492,989

(22) Filed: Jun. 11, 2012

(65) Prior Publication Data

US 2012/0308992 A1 Dec. 6, 2012

Related U.S. Application Data

(63) Continuation of application No. 12/161,561, filed as application No. PCT/DK2007/050005 on Jan. 19, 2007, now Pat. No. 8,198,073.

(60) Provisional application No. 60/759,952, filed on Jan. 19, 2006.

(30) Foreign Application Priority Data

Jan. 19, 2006 (DK) ................................ 2006 00083

(51) Int. Cl.
*C12Q 1/00* (2006.01)

(52) U.S. Cl.
USPC ................ 435/4; 422/50; 422/420; 422/421; 422/423; 422/429; 435/287.1; 435/287.7; 435/287.8

(58) Field of Classification Search
None
See application file for complete search history.

(56) References Cited

U.S. PATENT DOCUMENTS

| 3,418,079 | A | 12/1968 | Hans-Georg et al. |
| 3,547,780 | A | 12/1970 | Finnerty et al. |
| 3,875,013 | A | 4/1975 | Manautou et al. |
| 3,901,657 | A | 8/1975 | Lightfoot |
| 3,968,011 | A | 7/1976 | Manautou et al. |
| 4,215,995 | A | 8/1980 | Turk et al. |

(Continued)

FOREIGN PATENT DOCUMENTS

| AU | 634814 | 3/1993 |
| BE | 1011487 | 10/1999 |

(Continued)

OTHER PUBLICATIONS

English abstract of Magyar Aldatorvosok Lapia 1985.49, 6. 359-360. 359 "Rapid Determination of Urea Content in Milk as an Informatory Method for the Estimation of protein Energy Ratio of Consumed Feedstuff" Magdus Melinda and re-typed version thereof for clarity.

(Continued)

*Primary Examiner* — Chris L Chin
(74) *Attorney, Agent, or Firm* — Foley & Lardner LLP (57) ABSTRACT

A method of preparing a dry stick test device for determining an analyte in a milk sample by chemical assay. At least one reagent pad is provided by impregnating a first porous material with an aqueous solution including a reagent capable of reacting with the analyte, a derivative of the analyte or an indicator compound for the analyte to provide a detectable signal when in a moistened state. The reagent pad is dried. A development pad is provided by impregnating a second porous material with an aqueous solution including at least one controlling compound which, when in a moistened state, is capable of providing a condition required for the reagent to react with the analyte to provide the detectable signal. The impregnated second porous material is dried. The first porous material is immobilized with the second porous material, on a solid support, to obtain the dry stick test device.

20 Claims, 3 Drawing Sheets

U.S. PATENT DOCUMENTS

| | | | |
|---|---|---|---|
| 4,223,089 A | 9/1980 | Rothe et al. |
| 4,245,096 A | 1/1981 | Rothe et al. |
| 4,357,144 A | 11/1982 | Gindler et al. |
| 4,506,019 A | 3/1985 | Lee |
| 4,710,458 A | 12/1987 | Maines |
| 4,720,455 A | 1/1988 | Babu et al. |
| 4,732,736 A | 3/1988 | Kobayashi et al. |
| 5,219,730 A | 6/1993 | Potocnjak et al. |
| 5,260,219 A | 11/1993 | Fritz |
| 5,352,411 A | 10/1994 | Khuri |
| 5,370,994 A | 12/1994 | Stewart et al. |
| 5,411,858 A | 5/1995 | McGeehan et al. |
| 5,663,054 A | 9/1997 | Williams et al. |
| 5,697,326 A | 12/1997 | Mottram et al. |
| 5,698,083 A | 12/1997 | Glass |
| 5,776,779 A | 7/1998 | Tamura et al. |
| 5,932,431 A | 8/1999 | Williams et al. |
| 2003/0059951 A1 | 3/2003 | Frushour et al. |
| 2003/0073073 A1 | 4/2003 | Wolde-Mariam |

FOREIGN PATENT DOCUMENTS

| | | |
|---|---|---|
| DK | 198604261 | 9/1985 |
| EP | 0 282 192 A1 | 9/1988 |
| EP | 0 325 449 A2 | 7/1989 |
| EP | 0 339 331 A2 | 11/1989 |
| EP | 0 354 978 A2 | 2/1990 |
| EP | 0 458 231 | 11/1991 |
| EP | 0 577 092 A2 | 1/1994 |
| EP | 0 810 290 A2 | 12/1997 |
| EP | 0 810 436 | 12/1997 |
| EP | 0 902 287 A1 | 3/1999 |
| EP | 1 160 571 A1 | 12/2001 |
| EP | 0 990 706 | 9/2002 |
| EP | 1 321 478 | 6/2003 |
| GB | 2 023 815 A | 6/1979 |
| GB | 2 207 245 | 1/1989 |
| JP | 10-229023 | 8/1998 |
| JP | 2000-055921 A | 2/2000 |
| WO | WO-90/12487 A2 | 11/1990 |
| WO | WO-92/21980 | 12/1992 |
| WO | WO-93/03053 | 2/1993 |
| WO | WO-95/25282 A2 | 9/1995 |
| WO | WO 97/17375 A1 | 5/1997 |
| WO | WO-00/33074 | 6/2000 |
| WO | WO-03/023051 A2 | 3/2003 |
| WO | WO-03/093788 A2 | 11/2003 |
| WO | WO-2004/025301 A1 | 3/2004 |
| WO | WO-2005/057216 A1 | 6/2005 |

OTHER PUBLICATIONS

English abstract of Von H. Erbersdobler et al. "Schnelle Harnstoffbestimmung in Milch mit Hilfe Einer Teststreifen-methods und reflektometrischer Auswertung" Milchwissenscharf 41, 5, 1986.

European Search Report for International Application No. PCT/DK2007050005 dated Dec. 16, 2008.

L.A. Rodriguez et al., "Effect of Degradability of Dietary Protein and Fat on Ruminal, Blood, and Milk Components of Jersey and Holstein Cows." J. Dairy Sci. vol. 80, pp. 353-363, 1997.

S. Godden, DMV, et al., "Evaluation of the Azotest Strip as Recommended for the Estimation of Milk Urea Nitrogen Concentrations in individual Cow, Milk Line and Bulk Tank Samples."The Bovine Practitioner, vol. 37, No. 1, St. Paul, Minnesota.

Sen-Yuan Hwang et al. "Diurnal Variation in Milk and Blood Urea Nitrogen and Whole Blood Ammonia Nitrogen in Dairy Cows." Asian Australasian Journal of Animal Science, vol. 14, No. 12, pp. 1683-1689, 2001.

U.S. Appl. No. 12/161,561 Notice of Allowance dated Jan. 6, 2012.

U.S. Appl. No. 12/161,561 Office Action dated Jun. 1, 2011.

W.R. Butler et al., "Plasma and Milk Urea Nitrogen in Relation to Pregnancy Rate in Lactating Dairy Cattle."Journal of Animal Science, vol. 74, pp. 858-865, 1996.

DRY STICK DEVICE AND METHOD FOR DETERMINING AN ANALYTE IN A SAMPLE

CROSS-REFERENCE TO RELATED PATENT APPLICATIONS

Denmark Priority Application PA 2006 00083, filed Jan. 19, 2006 including the specification, drawings, claims and abstract, is incorporated herein by reference in its entirety. This application is a Continuation of U.S. application Ser. No. 12/161,561 (National Stage of PCT/DK2007/050005), filed Jan. 19, 2007, incorporated herein by reference in its entirety, which claims priority from Provisional Application U.S. Application 60/759,952, filed Jan. 19, 2006, incorporated herein by reference in its entirety.

FIELD OF THE INVENTION

The present invention relates to the field of analyzing an analyte in a sample. In particular the present invention relates to an improved construction of a dry stick device for the determination of an analyte in a sample by the use of a chemical assay, where care is particularly is taken to avoid precipitation of sample components on the top-face of the device causing limitation of the detectable signal.

PRIOR ART

Dairy Herd Improvement (DHI) has always been based on milk recording of individual cows in a herd. By increasing this knowledge of each individual cow, it is possible to both increase the quantity and to improve the quality of the milk Furthermore, the general health situation is improved and thereby the income for the farmers will increase. One way for the farmers to increase their income may be to optimize feeding by monitoring the content of urea.

In dairy cow farming, it is highly important that the animals (e.g. cows) utilize the protein content in the feed optimally, as protein is one of the most expensive feed components. The utilization depends, inter alia, on the amount of energy and protein simultaneously present in the animal.

When a feed contains more protein than is necessary, not all the ammonia formed there from can be processed in the rumen. The excess ammonia is taken up in the blood and discharged to the liver where the ammonia is converted to urea $(CO(NH_2)_2)$. This urea is taken up in the blood and largely excreted via the urine. From the blood, a small part of the urea also finds its way to the milk. In a cow producing 25 kg milk, the urea content is generally about 5 to 8 g urea pr. 25 kg milk or (0.2 to 0.3 g/l). The more ammonia in the rumen, the more urea in the blood, which again means more urea in the milk.

Excess of protein (which also provides excess of nitrogen, because protein includes nitrogen) in the feed leads to higher urea content in the milk. Accordingly, from the viewpoint of nitrogen utilization, a low urea content is desirable. However, there is also a lower limit. Unduly low urea content indicates an improper energy ratio in the feed or an unduly low protein content of the feed. If the animals are feed less it will produce less milk than they are capable of, and/or the protein content in the milk decreases. Another important point may be that it requires energy to process urea. In other words, a high nitrogen balance is also energetically unfavourable.

There is a direct relationship between the amount of protein fed and the concentration of urea in the blood and milk. High MUN (Milk Urea Nitrogen) results indicate an opportunity to reduce protein content of diets, without reducing the milk yield. This will reduce feeding costs and furthermore reduce nitrogen release to the environment. Overfeeding with protein, resulting in high urea levels in the milk, will have the following consequences:

Energy is needed for cows to synthesize urea for excretion
Reduction in the amount of energy available for milk production
Less available energy may put early lactation at increased risk of ketosis
High level of urea is toxic to sperm and embryos and can result in reduced fertility
High urea levels contribute to environmental contamination Today many farmers overfeed protein by 10-20%. Overfeeding protein by 20%, will lead to increased cost of about USD 50/cow/year. The information given to the farmers by watching the Milk Urea Nitrogen will provide the basis for decisions on how to change the feeding, especially concerning the energy/protein ratio (see the table below). Because MUN levels are affected by a large number of cow-related factors, including age, stage of lactation, health status, water consumption and dry matter intake, cows fed the same ration often have very different MUN values. Therefore it is generally recommend using MUN results from a minimum of 10 cows for diagnosing feeding problems.

All the information from milk samples provided on urea content, plus many other data on individual cows, may be stored in or on several databases. A number of databases could be linked together and used by consultants, veterinarians, advisors and others without the need for on-farm visits. The information can be used to compare the situation in different countries, to improve the breeding values, to optimize the feeding and to reduce the problem with insufficient feeding.

Thus, the determination of urea in a sample has become increasingly popular and new technologies allowing measurement on a large number of samples and Milk Urea Nitrogen (MUN) is often used as an indicator of ammonia levels in the rumen. The MUN content is a quick, accurate reflection of the amount of nitrogen absorbed by the cow but not used for growth or milk protein synthesis. Determination of the urea content in a sample employing enzyme based test devices like Reflotest and Azotest®Strip/Azostix are well known to a person skilled in the art. Both the Reflotest and Azotest®Strip/Azostix employ urease and azo dyes for the determination of urea in a sample.

The urea content in a sample may also be determined using a chemical assay utilising colouring agents such as o-phtalaldehyde, such chemical assays are as well known for the person skilled in the art. Often chemical assays involves compounds/controlling compounds (such as acids) which may cause precipitation of sample components.

U.S. Pat. No. 4,215,995 discloses test means for determining the content of urea in a sample. The test means involves a single filter paper which is impregnated in a three stage application of reagents (including o-phtalaldehyde) separated from each other on an acidic modified carrier matrix. In this way a higher stability of the reagents are achieved and precipitation of the serum proteins may be avoided by providing a suitable acid matrix by using a strong cation exchange loaded paper. The problem with the device provided by U.S. Pat. No. 4,215,995 is that the acidity component is not isolated from the reagents and will be contacted directly with pH sensitive liquid samples which may cause precipitation of sample components on the top-face of the device and thus reduce the readable signal.

Patent application JP 10-229023 discloses a test device comprising a solid support and a reagent pad and a developing pad for the determination of urea in a sample, such as blood, serum or plasma. The reagent pad is being impregnated with o-phthalaldehyde glycerine acetal, polyvinyl pyrolidone and distilled water. The developing pad is being impregnated with N-1-naphtyl-N'-diethylethylenediamine oxalate, 4-sulphophthalic acid in an aqueous solution, a surfactant and distilled water. The reagent pad is then coated onto the solid support and onto of this reagent pad is the developing pad coated. The problem of using this or a similar test device for the determination of urea in a sample such as milk is that the acid impregnated in the developing pad (the top layer) causes the milk proteins to precipitate on the top of the device. This precipitation interferes with the colour developed when urea is determined and may increase the numbers of false results.

Thus, there is a need in the industry for a simple dry stick construction where the interference from precipitated sample components is limited or avoided.

SUMMARY OF THE PRESENT INVENTION

Accordingly, in a first aspect, the aim of the present invention is to provide a dry stick test device for the determination of an analyte in a sample by means of a chemical assay wherein said dry stick device is constructed in such a manner so as to limit or avoid precipitation of sample component(s). The dry stick test device comprises:
(i) optionally a solid support,
(ii) at least one reagent pad comprising a reagent capable of reacting with the analyte, a derivative of said analyte or an indicator compound for said analyte to provide a detectable signal when in moistened state,
(iii) a development pad which is located in contact with the at least one reagent pad, optionally between the solid support and the at least one reagent pad, said development pad comprises at least one controlling compound capable of providing a condition required for the reagent to react with the analyte to provide a detectable signal,
wherein the at least one reagent pad and the development pad are arranged to avoid precipitation of sample component(s) on the top-face of the device.

In another aspect of the present invention a dry stick test device for the determination of an analyte in a milk sample by means of a chemical assay is provided. The dry stick test device comprises:
(i) optionally a solid support,
(ii) at least one reagent pad comprising a reagent capable of reacting with the analyte, a derivative of said analyte or an indicator compound for said analyte to provide a detectable signal when in moisten state,
(iii) a development pad which is located in contact with the at least one reagent pad, optionally between the solid support and the reagent pad, said development pad comprises at least one controlling compound capable of providing a condition required for the reagent to react with the analyte to provide a detectable signal,
wherein the at least one reagent pad is capable of providing a pH-value of the milk sample of 6 or above 6 in order to avoid precipitation of sample component(s), and the controlling compound present in the development pad is capable of providing a pH-value of the milk sample below 6.

Furthermore, it is an aspect of the present invention to provide a dry stick test device for the determination of urea in a sample, said dry stick test device comprises, optionally a solid support and at least 2 pads, said at least 2 pads comprises (i) at least one reagent pad comprising o-phthalaldehyde or a derivative thereof, a colouring compound and a detergent, and
(ii) a development pad comprising at least one acid, wherein the development pad is located down-stream from the at least one reagent pad.

It is also the aim of the present invention to provide a method for the preparation of the dry stick device according to the present invention. The method comprises the steps of:
(i) providing at least one reagent pad by impregnating a first porous material with an aqueous solution comprising a reagent capable of reacting with the analyte, a derivative of said analyte or an indicator compound for said analyte to provide a detectable signal when in a moistened state,
(ii) thereafter drying the at least one reagent pad,
(iii) providing a development pad by impregnating a second porous material with an aqueous solution comprising at least one controlling compound which, when in a moistened state, is capable of providing a condition required for the reagent to react with the analyte to provide a detectable signal,
(iv) thereafter drying the impregnated second porous material, and
(v) immobilizing the first porous material with the second porous material, optionally on a solid support, to obtain the dry stick device.

In a further aim of the present invention, a method for the determination of an analyte in a sample is provided. The method comprises the steps of:
(a) applying the sample suspected of containing the analyte to dry stick test device, said dry stick test device comprises:
(i) at least one reagent pad comprising a reagent capable of reacting with the analyte, a derivative of said analyte or an indicator compound for said analyte to provide a detectable signal when in a moistened state, and
(ii) in contact with said at least one reagent pad a development pad is located, said development pad comprises at least one controlling compound capable of providing a condition required for the reagent to react with the analyte to provide a detectable signal, wherein the at least one reagent pad and the development pad are arranged to avoid precipitation of sample component(s) on the top- face of the device.
(b) permitting the sample to migrate into the at least one reagent pad and the developing pad and mobilising the at least one reagent and the at least one controlling compound, and
(c) permitting the at least one reagent and the analyte, the derivative of said analyte or the indicator compound for said analyte to react and provide a detectable signal.

The present invention will now be described in more detail in the following.

DETAILED DISCLOSURE OF THE PRESENT INVENTION

The inventors of the present invention surprisingly found and developed a new construction of a dry stick test device wherein the interference from precipitated components from the sample is limited or avoided.

The new construction of the dry stick test device for the determination of an analyte in a sample by means of a chemical assay comprises: (i) optionally a solid support, (ii) at least one reagent pad comprising a reagent or a combination of reagents capable of reacting with the analyte, a derivative of said analyte or an indicator compound for said analyte to provide a detectable signal when in moistened state, (iii) a development pad which is located in contact with the at least one reagent pad, optionally between the solid support and the at least one reagent pad, said development pad comprises at least one controlling compound capable of providing a condition required for the reagent to react with the analyte to provide a detectable signal, In an embodiment of the present invention the at least one reagent pad comprises a reagent capable of reacting with the analyte, a derivative of said analyte or an indicator compound for said analyte and/or a reagent capable of participating in the determination of the analyte. The reagent capable of participating in the determination of the analyte may be a reagent taking part in the assay for providing a detectable signal, but which does not bind, react or interact directly with the analyte.

In the present context, the term "chemical assay" relates to the determination of the relative amount(s) of one or more components of the sample by means of a chemical and/or biochemical reaction. In an embodiment of the present invention the chemical assay involves the determination of the analyte which is not based on an enzyme-based determination.

An enzyme-based assay is an assay that depends on or uses enzymatic activity in order to produce a detectable signal.

As mentioned above the dry stick test device comprises at least one reagent pad and a development pad wherein the at least one reagent pad comprises the reagent or the combination of reagents and the development pad comprises at least one controlling compound capable of providing a condition required for the reagent or the combination of reagents to react with the analyte to provide a detectable signal. In an embodiment of the present invention the at least one reagent and the development pad are located relative to each other in such a manner that precipitation of sample components may be avoided, in particular, to avoid precipitation of sample components on the surface, where the reading/determination (of the colour) is being performed.

In the present context the term "arranged to avoid precipitation" relates to the placing of the at least one reagent pad and the developing pad in such a manner that precipitation of sample components on the top-face of the dry stick test device is avoided when applying the sample. Alternatively a compound which causes sample components not to precipitate could be added. By precipitation of sample components is meant sample components of the fluid sample or part of the fluid sample that change into a solid or semisolid mass, often caused by the action of e.g. heat or chemical substances. It is preferred that the precipitation is provided by the action of a chemical substance (in the present context a controlling compound).

In the present context the term "top face" relates to the surface of the uppermost pad of the dry stick device. Preferably, it relates to the surface of the dry stick device according to the present invention where the sample is applied or where the sample initially gets into contact with the development pad and/or the at least one reagent pad.

In an alternative embodiment of the present invention the term "top face" relates to the surface of the dry stick test device of the present invention from where the detectable signal may be obtained. This surface may be the same as the surface where the sample is applied or it may be a different surface.

In an embodiment of the present invention, the dry stick test device may comprise at least 2 reagent pads, such as at least 3 reagent pads, e.g. at least 4 reagent pads, such as at least 5 reagent pads, e.g. at least 6 reagent pads.

In the present context, the term "sample components" relates to all the substances present in the sample at the time of performing the assay, the "sample components" may in an embodiment of the present invention be one of the reagents of the assay. In an embodiment of the present invention the sample components that may tend to precipitate in e.g. a milk sample may be milk proteins, such as casein molecules. It is obvious to the person skilled in the art to identify other sample components in different kinds of samples that may tend to precipitate and then construct a dry stick test device suitable for this sample (and the sample components contained) based on the teaching provided herein.

The inventors of the present invention have also provided a new method for the determination of an analyte in a sample. The method comprises the steps of:
  (a) applying the sample suspected of containing the analyte to dry stick test device, said dry stick test device comprises:
    (i) at least one reagent pad comprising a reagent capable of reacting with the analyte, a derivative of said analyte or an indicator compound for said analyte to provide a detectable signal when in a moistened state, and
    (ii) in contact with said at least one reagent pad a development pad is located, said development pad comprises at least one controlling compound capable of providing a condition required for the reagent to react with the analyte to provide a detectable signal, wherein the at least one reagent pad and the development pad are arranged to avoid precipitation of sample component(s) on the top- face of the device.
  (b) permitting the sample to migrate into the at least one reagent pad and the developing pad and mobilising the at least one reagent and the at least one controlling compound, and
  (c) permitting the at least one reagent and the analyte, the derivative of said analyte or the indicator compound for said analyte to react and provide a detectable signal.

The detectable signal may be any substance which directly or indirectly is capable of being observed by any kind of visual or instrumental means. The instrumental means may be e.g. a magno(magne)tometer, spectrophotometer, ELISA-reader. Various suitable compounds may be suitable as the colour producing compound. In the present invention the colour producing compound may be selected from the group consisting of chromogens, catalysts, fluorescent compounds, chemiluminescent compounds, radioactive labels, metals, magnetic particles, dye particles, organic polymer latex particles, liposomes or other vesicles containing signal producing substances and the like.

In the present context the term "in a moistened state" relates to the contact between the reagents in the reagent(s) pad and/or the controlling compound in the development pad and the sample whereby the reagent(s) pad and/or the regulating pad becomes wet or slightly wet. The effect of the moistened state is that the dried reagents, the dried controlling compound(s) are liberated and dissolved (mobilised) and the reaction in the dry stick device commences and a detectable signal is produced, which is dependent on the amount of analyte present in the sample.

The Porous Material

The materials selected to be used in the at least one reagent pad and/or the development pad may be selected from a porous material. In the present context the term "porous material" relates to a material which adsorbs the sample and thereby permits it to migrate.

The porous material selected may comprise a pore-size and capacity that make it possible to provide a high flow-rate which quickly dissolves the reagent or the combination of reagents and which provides a good and substantially even distribution of the samples. Preferably, the porous material may be selected for providing substantially no retention of triglyceride rich samples. In an embodiment of the present invention the retention of triglycerides is 0%, such as at the most 1%, e.g. at the most 2.5%, such as at the most 5%, e.g. at the most 10%, such as at the most 15%, e.g. at the most 25%, such as at the most 50%, or the retention of most or all of the triglycerides, e.g. at the most 75%, such as at the most 100%.

The porous material is preferably selected from the group consisting of a nitrocellulose membrane, cellulose, a polymer (such as nylon, polyvinylidene fluoride or latex), glass fibre, woven fibres, non-woven fibres, a chromatographic gel membrane, diatomaceous earth, silica gel, silicium oxide and kieselguhr.

In an embodiment of the present invention, the porous material in the at least one reagent pad and/or in the development pad may be selected from a group of materials comprising a pore size preferably in the range of 1-1000 μm, such as in the range of 1-500 μm, such as in the range of 1-100 μm, for instance in the range of 1-75 μm, such as in the range of 5-500 μm, such as in the range of 5-100 μm, for instance in the range of 5-75 μm, such as in the range of 10-500 μm, such as in the range of 10-100 μm, for instance in the range of 10-75 μm, such as in the range of 10-50 μm, for instance in the range of 50-200 μm, such as in the range of 50-100 μm, for instance in the range of 100-500 μm, such as in the range of 50-300 μm, for instance in the range of 75-300 μm, such as in the range of 75-200 μm, for instance in the range of 75-150 μm, such as in the range of 75-120 μm.

In yet another embodiment of the present invention, the porous material in at least one reagent pad and/or in the development pad may be selected from a group of materials comprising a suitable pore size such as at most 500 μm, for instance at most 200 μm, such as at most 150 μm, for instance at most 100 μm, such as at most 75 μm.

Preferably, the porous materials used in the at least one reagent pad and/or the development pad may be the same in at least 2 pads, such as at least 3 of the pads, for instance 4 of the pads, such as at least 5 of the pads.

In accordance with the above porous material, it may be desirable to provide a device for detecting an analyte in a fast assay. In an embodiment of the present invention the assay time at approximately 20° C. may be less than 20 minutes, such as less than 18 minutes, e.g. less than 15 minutes, such as less than 12 minutes, e.g. less than 10 minutes, such as less than 8 minutes, e.g. less than 5 minutes, such as less than 3 minutes, e.g. less than 2 minutes, such as in the range of 1 to 25 minute, e.g. in the range of 2-25 minutes, such as in the range of 5 to 20 minute, e.g. in the range of 8-18 minutes, such as in the range of 10 to 15 minute, e.g. in the range of 11-14 minutes, such as in the range of 12-13 minutes.

The Solid Support

The device according to the present invention may be supported by a solid support. In the present context, the term "solid support" refers to a material, which has no influence on the migration or on the reaction of the liquid sample or on reagent(s) or the agents capable of increasing the rate of the reaction. The solid support provides a stabilising basis for the assay device and provides sufficient strength to maintain the desired physical shape and has substantially no interference with the production of a detectable signal.

In an embodiment of the present invention, the material for the solid support is selected from the group consisting of tubes, polymeric beads, nitrocellulose strips, membranes, filters, plastic sheets and the like.

Naturally, synthetic and natural occurring materials that are synthetically modified can be used as the material of the solid phase. Such materials include polysaccharides, for instance cellulosic materials such as paper and cellulosic derivatives, such as cellulose acetate and nitrocellulose, silica-orinorganic materials, such as, for example, deactivated alumina, diatomaceous earth, $MgSO_4$ or other inorganic finely divided material uniformly dispersed in a porous polymeric matrix, wherein the matrix may comprise one or more polymers such as homopolymers and copolymers of vinyl chloride, for instance, polyvinyl chloride, vinyl chloride-propylene copolymer, and vinyl chloride-vinyl acetate copolymer, cloth, both naturally occurring (for instance, cotton) and synthetic (for instance, nylon), porous gels, such as silica gel, agarose, dextran, and gelatin, polymeric films, such as polyacrylamide, and the like.

In an embodiment of the present invention, the solid support may be omitted from the dry stick test device. In this case the dry stick test device comprises at least one reagent pad and a development pad. When performing a determination of an analyte using a dry stick test device without a solid support, the sample may be applied to the dry stick test device on one surface and the detectable signal may be detected on the same or another surface, thus it is preferred that any possible precipitation of sample components on the surface where the detectable signal are to be detected may be limited or avoided.

The Reagent Pad

In the present context the term "reagent pad" relates to one or more pads comprising a reagent or a combination of reagents. The reagent or the combination of reagents may preferably be impregnated into the reagent pad in such a manner that the reagent or the combination of reagents is/are immobilised when in dry state and mobile when in moistened state.

In the present context of the present invention the term "reagent" relates to the chemical substance that reacts with or participate in or is necessary for the determination of an analyte, a derivative of said analyte or an indicator compound for said analyte to provide a detectable signal. A similar definition of the combination of reagents may be provided which relates more specifically to 2 or more reagents, such as 3 or more reagents, e.g. 4 or more reagents, such as 5 or more reagents, e.g. 6 or more reagents.

In an embodiment of the present invention the dry stick test device comprises at least 2 reagent pads, such as at least 3 reagent pads, e.g. at least 4 reagent pads, such as at least 5 reagent pads, e.g. at least 6 reagent pads. In this embodiment the reagents that reacts with or participate in or is necessary for the determination of an analyte, a derivative of said analyte or an indicator compound for said analyte to provide a detectable signal may be introduced into different reagent pads. This may improve stability, storage 15 properties and applicability of the dry stick device because non-compatible compounds can be included in different reagent pads of the dry stick device.

The Development Pad

In the present context, the term "development pad" relates to a pad capable of regulating the environment and the conditions for the sample comprising the analyte to an environment that facilitates the determination of the analyte, a derivative of said analyte or an indicator compound for said analyte.

In an embodiment of the present invention, the development pad may comprise one or more controlling compounds capable of increasing the rate of the reaction between the analyte, a derivative of said analyte or an indicator compound for said analyte present in the sample and the reagent(s). In an embodiment of the present invention the controlling agent may be an acid or a base.

In yet another embodiment of the present invention, the development pad is in contact with at least one reagent pad by substantially fully overlapping, by partial overlap or by laying adjacent to at least one reagent pad. In an embodiment of the present invention the development pad is overlapping the at least one reagent pad by at least 5%, such as at least 10%, e.g. at least 25%, such as at least 50%, e.g. at least 75%, such as at least 80%, e.g. at least 90%, such as at least 95%. In the present context the term "substantially fully overlapping" relates to two separate pads (the development pad and the at least one reagent pad) being placed on top of one another. In the present context the term "partial overlap" relates to two separate pads (the development pad and the at least one reagent pad) being overlapping with only part of the pad(s). A partial overlap of 100% relates to a full overlap and a deviation of 5% from the 100% full overlap relates to a substantially full overlap.

In an embodiment of the present invention the development pad and the at least one reagent pad(s) are laying adjacent to one another. This means that the pads are placed in contact with each other (touching each other). An overlap of 0% (but in contact) relates to the term "laying adjacent", furthermore, an overlap of less than 5% is considered being within the term of "laying adjacent", such as an overlap of at the most 4%, e.g. an overlap of the most 3%, such as an overlap of the most 2% or e.g. an overlap of the most 1%.

Controlling Compound

In the development pad a controlling compound is immobilised. In the present context the term "controlling compound" relates to a substance that has the function as a propellant or a fuel in the specific assay for the determination of the analyte, a derivative of said analyte or an indicator compound for said analyte. The controlling compound may also be the chemical substance responsible for the precipitation of sample components or the chemical compound causes the sample components not to precipitate. In an embodiment of the present invention the controlling compound may be separated from at least one of the reagents in order to improve the stability of the dry stick test device.

In yet another embodiment of the present invention the controlling compound may be an acidic or an alkaline compound. Preferably, the controlling compound is an acidic compound capable of providing a pH-value of the sample in the dry stick test device, when in a moistened state, below pH 6, such as below pH 5, e.g. below pH 4, such as below pH 3, e.g. below pH 2, such as below pH 1, e.g. below pH 0, such as in the range of pH 0-6, e.g. in the range of pH 0-5, such as in the range of pH 0-4, e.g. in the range of pH 0-3, such as in the range of pH 0-2, e.g. in the range of pH 0-1, such as in the range of pH 1-6, e.g. in the range of pH 2-6, such as in the range of pH 3-6, e.g. in the range of pH 4-6, such as in the range of pH 5-6.

In another embodiment of the present invention the controlling compound may be an alkaline compound capable of providing a pH-value of the sample in the dry stick test device, when in a moistened state, of pH 8 or above, such as in the range of pH 8-14, e.g. in the range of pH 8-13, such as in the range of pH 8-12, e.g. in the range of pH 8-11, such as in the range of pH 8-10, e.g. in the range of pH 8-9, such as in the range of pH 9-12, e.g. in the range of pH 10-13, such as in the range of pH 10-11.

The Analytes to be Determined

A device or a method based on the above principles can be used to determine a wide range of analytes by choice of appropriate colouring compounds known to the person skilled in the art, and the invention need not be limited to examples mentioned herein.

In an embodiment of the present invention the analytes to be assayed can be selected from the group consisting of a protein, a fat, a carbohydrate, an antibiotic, a steroid, such as hormones, a vitamin, a chemical compound, a hapten, a cell, such as a bacteria or such as leukocytes, an antibody, a drug of abuse and blood.

In a preferred embodiment of the present invention, the analyte is a chemical compound and the chemical compound may be selected from the group consisting of urea, triglyceride and ketone bodies, such as acetoacetate, beta-hydroxybutyrate (BHB), acetone, ascorbic acid, nitrates, urobilinogen, cholesterol, and steroids such as pregnenolone, progesterone, testosterone, dihydrotestosterone, estrone, estradiol, Cortisol, cortisone, aldosterone, corticosterone, androstenedione, 17α-OH-pregnenolone, 17α-OH-progesterone, 11-desoxycorticosterone, 11-desoxycortisol and dehydroepiandrosterone, luteinising hormone or human chorionic gonadotropin.

The device and the method according to the present invention may also be suitable when the analyte is a carbohydrate and the carbohydrate may be selected from the group consisting of a monosaccharide, such as glucose or galactose, and a disaccharide, such as lactose.

In a preferred embodiment of the present invention the dry stick test device is used for the determination of urea in a sample. The dry stick test device may comprises, optionally a solid support and at least 2 pads, said at least 2 pads comprises (i) at least one reagent pad comprising o-phthalaldehyde or a derivative thereof, a colouring compound and a detergent, and (ii) a development pad comprising at least one acid, wherein a development pad may be located down-stream from the at least one reagent pad. In this embodiment the acidic compound is capable of providing a pH-value of the sample in the dry stick test device, when in a moistened state below pH 6, such as below pH 5, e.g. below pH 4, such as below pH 3, e.g. below pH 2, such as below pH 1, e.g. below pH 0, such as in the range of pH 0-6, e.g. in the range of pH 1-5, such as in the range of pH 1-4, e.g. in the range of pH 1-3, such as in the range of pH 1-2, e.g. in the range of pH 2-6, such as in the range of pH 3-6, e.g. in the range of pH 4-6, such as in the range of pH 5-6. Preferably, the at least one reagent pad is in contact with the development pad by substantially fully overlapping, by partial overlap or by laying adjacent. It is also preferred that the development pad may be located between the solid support and the at least one reagent pad.

The Samples to be Analysed

In the present context, the term "a sample" relates to any sample found in the form of liquid, solid or gas and which may be liquefied at the time of assaying. In order to wet the porous material used in the development pad and/or in the at least one reagent pad to permit migration, a liquid sample may be applied. Furthermore, it is preferred that a minimum number of handling steps, of the liquid sample is necessary before applying it to the dry stick test device. In the present context, the term "handling steps" relates to any kind of pre-treatment of the liquid sample before or after it has been applied to the assay device. This pre-treatment comprises separation, filtration, dilution, distillation, concentration, inactivation of interfering compounds, centrifugation, heating, fixation, addition of reagents, or chemical treatment.

In an embodiment of the present invention the sample may be collected from a mammal, preferably the mammal is selected from the group consisting of herd animals, cows, camels, buffaloes, pigs, horses, deer, sheep, goats, pets, dogs, cats and humans.

In a preferred embodiment of the present invention, the sample can be derived from any desirable source, however, it is preferred that the sample is selected from the group consisting of milk, blood, serum, plasma, saliva, urine, sweat, ocular lens fluid, cerebral spinal fluid, ascites fluid, mucous fluid, synovial fluid, peritoneal fluid, amniotic fluid or the like.

Besides physiological fluids, other liquid samples such as various water samples, food products and the like can be used. In addition, a solid test sample can be used once it is modified to form a liquid sample, for instance in the form of a solution, a suspension or an emulsion.

In a preferred embodiment of the present invention a dry stick test device for the determination of an analyte in a milk sample by means of a chemical assay is provided. The device comprises:

(i) optionally a solid support,
(ii) at least one reagent pad comprising a reagent capable of reacting with the analyte, a derivative of said analyte or an indicator compound for said analyte to provide a detectable signal when in moisten state,
(iii) a development pad which is located in contact with the at least one reagent pad, optionally between the solid support and the at least one reagent pad, said development pad comprises at least one controlling compound capable of providing a condition required for the reagent to react with the analyte to provide a detectable signal, wherein the at least one reagent pad is capable of providing a pH-value of the milk sample of 6 or above 6 (preferably when in a moisten state), and the controlling compound present in the development pad is capable of providing a pH-value of the milk sample below 6 (preferably when in a moisten state).

In this embodiment the acidic compound is capable of providing a pH-value of the sample in the dry stick test device, when in a moistened state in the range of pH 1-5, such as in the range of pH 1-4, e.g. in the range of pH 1-3, such as in the range of pH 1-2, e.g. in the range of pH 2-5, such as in the range of pH 3-5, e.g. in the range of pH 4-5, such as in the range of pH 5-6. Preferably, the at least one reagent pad is in contact with the development pad by substantially fully overlapping, by partial overlap or by laying adjacent. It is also preferred that the development pad may be located between the solid support and the at least one reagent pad.

The Ancillary Compound

Because of the complexity of the liquid samples to be assayed in the present invention it may occasionally be an advantage to use an ancillary compound in order to improve the flow and adsorption of the liquid sample in the regulation pad and/or in the one or more reagent pad(s) and to provide a fast, consistent and even release of the reagent(s) and the agents capable of increasing the rate of reaction. The ancillary compound may be supplied to the device either by a) adding it to the at least one reagent pad(s) and/or regulation pad alone or together with the liquid sample, b) incorporating the ancillary compound into at least one of the reagent pad(s) and/or the regulation pad, or c) a combination thereof.

In an embodiment of the present invention, the ancillary compound is added to the dry stick device before the liquid sample is added. Preferably the ancillary compound is a liquid.

In another preferred embodiment of the present invention, the ancillary compound and the liquid sample are added to the dry stick device in layers. In the present context, the term "layers" refers to the splitting up of the volume of the ancillary compound and the volume of the liquid sample, and then the ancillary compound and the liquid sample are added to the first zone one after another. In this case, the ancillary compound may be added as a liquid as well as a solid compound. In an embodiment of the present invention, the ancillary compound and the liquid sample are split into at least 2 volumes each providing 4 alternating layers of ancillary compound and liquid sample, e.g. the ancillary compound and the liquid sample are split into at least 3 volumes each providing 6 alternating layers of ancillary compound and liquid sample, such as the ancillary compound and the liquid sample being split into at least 4 volumes each providing 8 alternating layers of ancillary compound and liquid sample, e.g. the ancillary compound and the liquid sample are split into at least 6 volumes each providing 12 alternating layers of ancillary compound and liquid sample, such as the ancillary compound and the liquid sample is split into at least 8 volumes each providing 16 alternating layers of ancillary compound and liquid sample, e.g. the ancillary compound and the liquid sample are split into at least 10 volumes each providing 20 alternating layers of ancillary compound and liquid sample, such as the ancillary compound and the liquid sample being split into at least 20 volumes each providing 40 alternating layers of ancillary compound and liquid sample.

In yet an embodiment of the present invention the ancillary compound may be impregnated into at least one reagent pad(s) and/or into the regulation pad.

In another embodiment of the present invention at least one reagent pad and/or the development pad incorporating at least one ancillary compound capable of improving the flow of the liquid sample.

In yet another embodiment of the present invention the ancillary compound provides a fast, consistent and homogenous release of the reagent(s) in the at least one reagent pad and/or the agent capable of increasing the rate of reaction in the development pad. Additionally, the ancillary compound provides low affinity for protein binding.

Furthermore, the ancillary compound may provide low retention of triglyceride rich samples and/or decreases the viscosity of the sample.

In an embodiment of the present invention the ancillary compound contains chemical constituents selected from the group consisting of water, a surfactant, a salt, a metal, a sugar, a protein, a solvent and a lipid.

Preparation of the Dry Stick

The dry stick device according to the present invention may be prepared by any conventional methods provided for the preparation of dry stick devices. In a preferred embodiment the method for providing a dry stick device according to the present invention comprises the steps of:
(i) providing at least one reagent pad by impregnating a first porous material with an aqueous solution comprising a reagent capable of reacting with the analyte, a derivative of said analyte or an indicator compound for said analyte to provide a detectable signal when in a moistened state,
(ii) thereafter drying the at least one reagent pad,
(iii) providing a development pad by impregnating a second porous material with an aqueous solution comprising at least one controlling compound which, when in a moistened state, is capable of providing a condition required for the reagent to react with the analyte to provide a detectable signal,
(iv) thereafter drying the impregnated second porous material, and
(v) immobilizing the first porous material with the second porous material, optionally on a solid support, to obtain the dry stick device.

In an embodiment of the present invention the at least one reagent pad is located relative to the development pad to avoid precipitation of a sample component on the top-face of the device. Preferably, the development pad is located between the solid support and the at least one reagent pad. The sample component may as described earlier be selected from the group consisting of proteins, carbohydrate, fat, cells, or other components present in the sample.

In yet an embodiment of the present invention the first porous material may be impregnated with o-phthalaldehyde or a derivative thereof and a colouring compound. Furthermore, the first porous material may be further impregnated with a detergent.

In another embodiment of the present invention the first porous material may comprise 1, 2 or 3 different porous materials having 3, 2 or 1 reagents impregnated, respectively. The reagents in this embodiment are selected from o-phthalaldehyde or a derivative thereof, a colouring compound and a detergent.

In an embodiment of the present invention the second porous material may be impregnated with an acid. Said acid may be capable of providing a pH-value of the sample in the dry stick test device, when in a moistened state below pH 6, such as below pH 5, e.g. below pH 4, such as below pH 3, e.g. below pH 2, such as below pH 1, e.g. below pH 0, such as in the range of pH 0-6, e.g. in the range of pH 0-5, such as in the range of pH 0-4, e.g. in the range of pH 0-3, such as in the range of pH 0-2, e.g. in the range of pH 0-1, such as in the range of pH 1-6, e.g. in the range of pH 2-6, such as in the range of pH 3-6, e.g. in the range of pH 4-6, such as in the range of pH 5-6.

In an embodiment of the present invention the second porous material may be impregnated with one or more reagent(s) capable of reacting with the analyte, a derivative of said analyte or an indicator compound for said analyte to provide a detectable signal when in a moistened state, preferably together with the controlling compound.

Additionally Embodiments

In an embodiment the dry stick test device according the present invention is used for the determination of an analyte in a sample. Preferably, the analyte is selected from the group consisting of a protein, a fat, a carbohydrate, an antibiotic, a steroid, a vitamin and a chemical compound. Preferably, the chemical compound is selected from the group consisting of urea, triglyceride and ketone bodies, such as acetoacetate, beta-hydroxybutyrate (BOHB), ascorbic acid (citric acid) and acetone. If the analyte is a carbohydrate the carbohydrate may be selected from the group consisting of glucose and lactose.

Determination of Urea

As mentioned above the determination of protein utilisation may be an important parameter. As it is the case in cattle farming, it is highly important that the animals (e.g. cows) optimally utilize the protein contained in the feed, because protein is one of the most expensive feed components. The utilization depends, inter alia, on the amount of energy and protein simultaneously present in the animal.

The new construction of the dry stick test device according to the present invention may be very useful for the qualitative and quantitative determination of urea in a sample, such as milk.

The one or more reagent pad(s) of the dry stick test device may be impregnated with o-phthalaldehyde or a derivative thereof and a colouring compound and optionally a detergent, such as a polyoxyethylene alkyl phenyl ether or a polyoxyethylene alkyl ether.

The derivative of o-phthalaldehyde of the present invention means a compound which is converted to o-phthalaldehyde after the derivative is dissolved in a liquid sample. The derivative includes o-phthalaldehyde glycerol acetal.

The colouring compound includes N-1-naphthyl ethylenediamine, N-1-naphthyl-N'-diethylethylenediamine and a salt thereof, such as salts of hydrochloric acid or oxalic acid are included.

The detergent may be a polyoxyethylene alkyl phenyl ether or a polyoxyethylene alkyl ether such as polyoxyethylene (9.5)p-t-octylphenylether (HLB: 13.5; Tradename: TRITON X-IOO), polyoxyethylene(40)p-t-octylphenylether (HLB: 17.9; Tradename: TRITON X-405), polyoxyethylene(20)octylphenylether (HLB: 16.2; Tradename: NISSAN NONION HS-220), polyoxyethylene(23)laurylether (HLB: 15.3; Tradename: Brij35), polyoxyethylene(20)palmitylether (HLB: 15.7; Tradename: Brij58), polyoxyethylene(20)laurylether (HLB: 16.2; Tradename: NISSAN NONION K-220), polyoxyethylene(20)stearylether (HLB: 15.3; Tradename: NISSAN NONION S-220), and so on.

The polyoxyethylene alkyl phenyl ether or polyoxyethylene alkyl ether of the present invention may have an HLB of 8 or more. In the present context, the term "HLB" relates to the Hydrophilic-Lipophilic Balance of the surfactant. This provides an indication of the hydrophilic portion of the molecule. More hydrophilic groups enable more solubility in water as more hydrogen bonds exist herein.

In an embodiment of the present invention, the development pad is impregnated with an acid necessary for the determination of urea. The acid used may be any kind of acid capable of providing and keeping a pH-value at 2.0 or lower when dissolved by the liquid sample. In particular, such acids include 4-sulfophthalic acid or an acid polymer.

The respective amount of o-phthalaldehyde or its derivative, the colouring compound (in the at least one reagent pad) and the acid (in the development pad) may be the amount which is necessary for the determination of urea in the specific assay. This means that the amounts are similar to those conventionally used for o-phthalaldehyde or its derivative, the colouring compound and the acid in the quantitative determination of urea. Normally, but not limited hereto, the amount of o-phthalaldehyde or its derivative is in the range sufficient to provide an amount of 0.05M-2M when the o-phthalaldehyde or its derivative are dissolved in the liquid sample. The amount of acid provided in the development pad may be sufficient to provide and keep the pH-value of the liquid sample at 2.0 or lower, when the liquid sample is being dissolved in the sample.

The amount of detergent may by sufficient to provide an amount of 0.1-20% (w/v) when the detergent becomes dissolved in the liquid sample, such as in an amount of 0.1-10% (w/v), e.g. in an amount of 4-10% (w/v). In an embodiment of the present invention, the amount of detergent, when dissolved in a liquid sample, can be calculated based upon the capacity of the sample kept in the dry stick test device.

Other known additives may be added to the dry stick test device which includes stabilisers, such as a surfactant etc. The surfactant may be used to improve extendibility and solubility of the liquid sample and to enhance the coating properties of the liquid solution(s) upon production. In an embodiment of the present invention the amount of a specified surfactant may be the same as the amount conventionally used.

The structure of the dry stick test device of the present invention is not limited except that it should contain o-phthalaldehyde or its derivative, a colouring compound and an acid separated into at least one reagent pad and a development pad wherein the at least one reagent pad and the development pad are arranged to avoid precipitation of sample component(s) on the top-face of the device. The dry stick test device of the present invention may be produced in a manner similar to the production of conventional test pieces for measuring urea or as described in this document.

In an embodiment of the present invention the dry stick test device may be provided with a plurality of reagent pads where different reagent(s) is/are comprised in each reagent pad. Furthermore, an intermediate pad may be provided between the pluralities of reagent pads. In yet an embodiment of the present invention the reagents may not all be comprised in the at least one reagent pad, but one or more of the reagent(s) may be comprised in the development pad.

Figure 1:
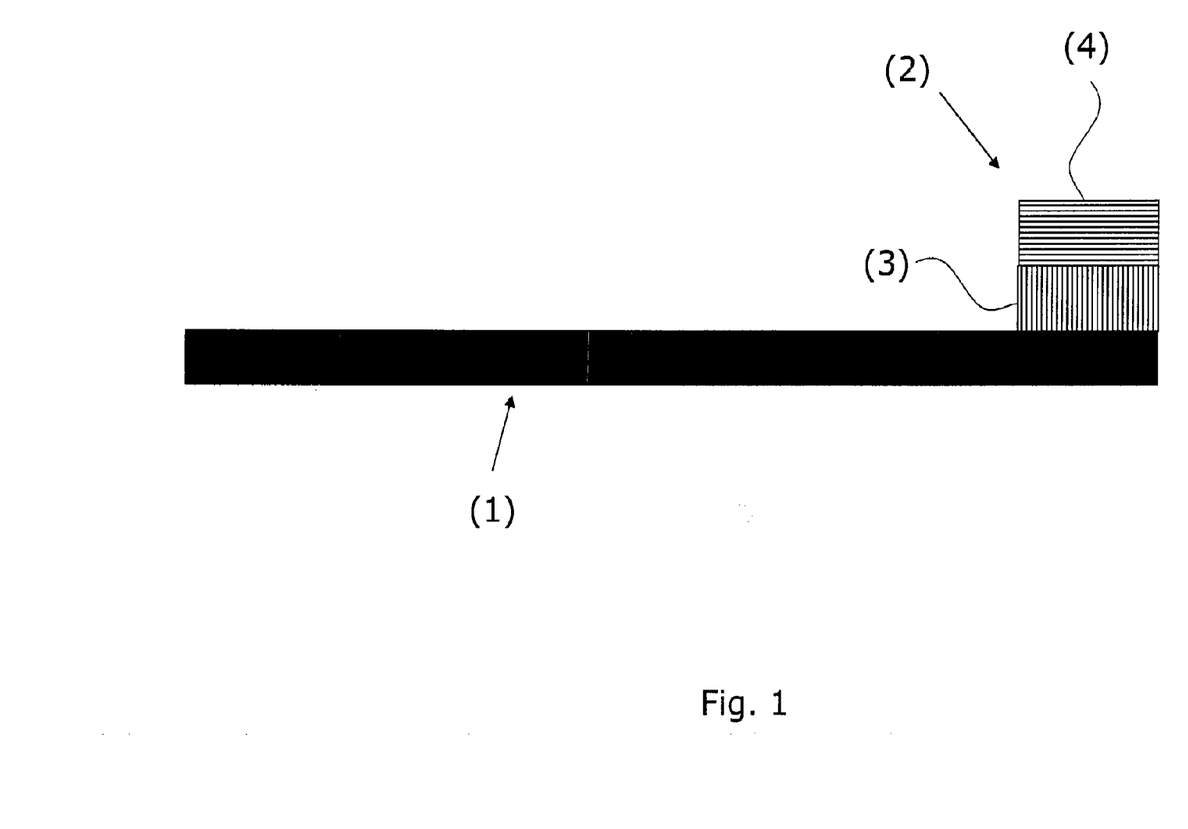
FIG. 1 shows one possible construction of the dry stick test device according to the present invention where (1) relates to the dry stick test device, (2) relates to the reagent section, (3) relates to the development pad and (4) relates to the reagent pad.

In FIG. 1, an example of the dry stick test piece is provided. The dry stick test piece comprises a solid support (1) having in one end a reagent section (2). The reagent section (2) comprises a development pad (3) located on the solid support (1) and on top of the development pad (3) is a reagent pad (4). In this example the liquid sample is applied to the reagent pad (4) and the reagents (comprised herein are dissolved and migrates throughout the reagent pad and to the development pad (4) thereby dissolving the acid comprised herein and the reaction for determining urea progresses.

When a predetermined amount of a liquid sample such as milk is dropped on the reagent pad (4) of the dry stick test piece (1), the sample is at first uniformly spread over the entire surface and throughout the entire reagent pad (4). The spread sample reaches the development pad (4) whereby the acid comprised in the development pad (4) is dissolved and the reaction proceeds. Urea determination comprised in the liquid sample reacts with o-phthalaldehyde or its derivative present in the reagent pad (4) to produce 1,3.dihydroxyisoindrin (DHI). The carbonium ion of the resulted DHI reacts with a colouring compound from the reagent pad (4) under acidic conditions, provided by the compound present in the development pad (3), to produce a colour—a detectable signal. With the progress of the reaction the reagents comprised in the reagent pad (4) and the acid comprised are substantially completely dissolved and dispersed into the development pad (3) thereby dissolving the acid comprised therein, and the reagent pad and the development pad form in combination a detection pad.

It is obvious for the person skilled in the art that the controlling compound and the construction of the dry stick test device may be changed based on the concept of the present invention, if a different assay is to be provided or is another analyte is being assayed.

Furthermore, it is also obvious for the skilled person how to choose the controlling compound to optimize the construction of the dry stick test device based on the knowledge provided by the concept of the present invention, namely, separating the controlling compound from the reagents (at least some of them) in different pads and subsequently arranging these pads in order to avoid precipitation of sample components, whereby the influence on the signal detected may be limited or avoided.

The concept of the present invention will be further illustrated in the following non-limiting figures and examples.

EXAMPLES

Example 1

Influence of Precipitation on Light Diffusion on Urea Dry Sticks

Experimental Set Up:

Pads comprising a strongly acidic bottom layer (development pad) and a dyed top layer (reagent pad) are mounted either with development pad up or with the reagent pad up. Milk samples are applied and the distribution of milk in the pads is described. At the end of incubation/reaction the pads are scanned and green colour is measured in order to calculate influence of precipitation on light diffusion on pads.

Preparation of Urea Dry Sticks:

Urea dry sticks (pads in plastic frames, lot number 20060928-1, produced according to "Production of UREA sticks ver. 4.0.2") comprising pads of $5 \times 5$ mm$^2$ are employed. Said pads consisting of two layers glued together, comprising:

1. a top layer comprising filterpaper impregnated with Triton X-405, N,N-diethyl-N'-1-Naphtyl-ethylenediamine Oxalate, the acetal of Glycerol and ortho-Phthaldialdehyde (reagent pad) and,
2. a bottom layer consisting of woven textile (nylon/PET) impregnated with 4-Sulfophthalic Acid (development pad).

The glued layers are cut into square pads, 5 by 5 mm$^2$ and placed in plastic frames either with the development pad on top of the reagent pad (inverted mounted) or with the reagent pad on top of the development pad (correctly mounted).

Preparation of Milk Samples:

Two milk samples (in the following numbered #11 and #14) were enriched with 500 mg/ml urea.

Performance Test of Correctly and Inverted Mounted Urea Dry Sticks:

Four correctly mounted sticks and four inverted sticks were fastened by tape.

8 µl milk #11 and 8 µl milk #14 was applied on two inverted urea dry sticks separately and on two correctly mounted urea dry sticks separately. Following incubation at 25° C. in 12 minutes and 30 seconds each urea dry stick was scanned inverted by Canon scanner ConoScan "2400U".

Figure 2:
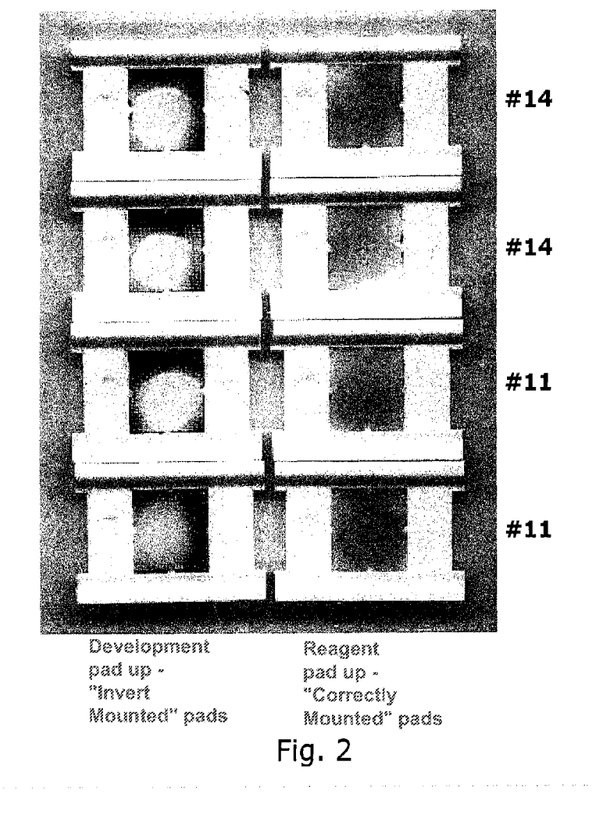
FIG. 2 shows dry stick test devices wherein the reagent pad is placed on top of the development pad and dry stick test devices wherein the development pad is placed upon the reagent pad. The pictures show different degrees of milk precipitation (white spots) on the reagent pad and development pad respectively.
Figure 3:
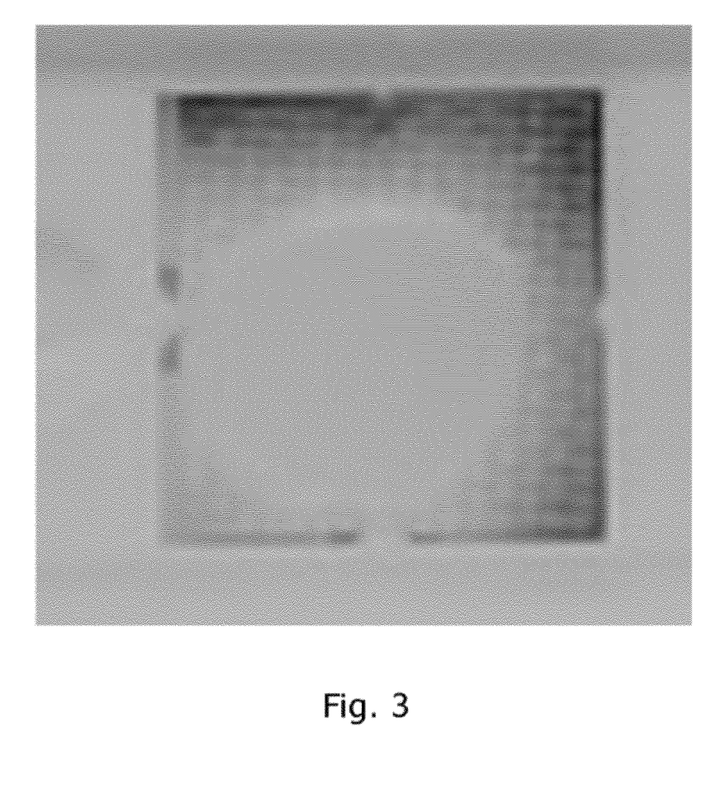
FIG. 3 shows a magnification of the upper left reagent pad of FIG. 2.

On urea dry sticks comprising correctly mounted pads, milk is easily spread and enters freely into the pad. Following incubation colour is uniformly spread over the entire surface. On urea dry sticks comprising inverted mounted pads, the 8 µl milk remains as a small drop, slowly releasing liquid into the pad. Next to incubation coagulated milk constituents (protein ("cheese") with fat globules) remain on the pad surface, forming a white spot covering approx. $\frac{2}{3}^{rds}$ of the area (See FIGS. 2 and 3).

Each of the eight scanned pads (with 300 dots per inch) was measured using Matlab software, a routine programme using red, green and blue colour. The field measured on each urea dry stick constitutes approx. 4×4 mm² as the pads edges was left out.

In the table below green colour values are shown.

| Pad orientation | | Average green | Standard deviation of pixels (green color) |
|---|---|---|---|
| Development pad up "inverted" | first sample #14 | 213.2 | 25.6 |
| | second sample #14 | 209.7 | 30.1 |
| | first sample #11 | 205.3 | 35.4 |
| | second sample #11 | 194.5 | 36.6 |
| Reagent pad up "correct" | first sample #14 | 204.3 | 5.1 |
| | second sample #14 | 213.7 | 8.7 |
| | first sample #11 | 206.1 | 5.8 |
| | second sample #11 | 199.4 | 5.1 |

Conclusion:

The above results clearly show, that the standard deviation of pixels (green color) is significantly higher (5-6 times) when pads are oriented with development pad up (inverted mounted pads) compared to pads with reagent pad up (correctly mounted pads). The results show that the color produced is not evenly distributed which cause false readings of the stick when the pads are mounted inverted and confirms that milk coagulates/precipitates significantly influence the assay and significantly influence dry stick performance.

REFERENCES

U.S. Pat. No. 4,125,995
JP 10-229023

What is claimed is:

1. A method for the preparation of a dry stick test device for the determination of an analyte in a milk sample by means of a chemical assay, said method comprising the steps of:
   (i) providing at least one reagent pad by impregnating a first porous material with an aqueous solution comprising a reagent capable of reacting with said analyte, a derivative of said analyte or an indicator compound for said analyte to provide a detectable signal when in a moistened state,
   (ii) thereafter drying said reagent pad,
   (iii) providing a development pad by impregnating a second porous material with an aqueous solution comprising at least one controlling compound which, when in a moistened state, is capable of providing a condition required for said reagent to react with said analyte to provide said detectable signal,
   (iv) thereafter drying said impregnated second porous material, and
   (v) immobilizing said first porous material with said second porous material, on a solid support, to obtain said dry stick test device, said dry stick test device comprising:
   said reagent pad comprising said reagent capable of reacting with said analyte, said derivative of said analyte, or said indicator compound for said analyte to provide said detectable signal when in a moistened state, and
   said development pad which is located in contact with said reagent pad, said development pad comprising said controlling compound capable of providing said condition required for said reagent to react with said analyte to provide said detectable signal, wherein said development pad is located downstream from said reagent pad,
   wherein said reagent pad and said development pad are arranged to avoid precipitation of a sample component on a top-face of said dry stick test device and wherein said milk sample is applied on said top-face of said dry stick test device and said detectable signal is obtained from said top-face of said dry stick test device, and
   wherein said controlling compound is an acidic compound and wherein said top-face of said dry stick test device relates to a surface where said milk sample initially contacts said reagent pad.

2. A method according to claim 1, wherein said dry stick test device comprises at least 2 reagent pads.

3. A method according to claim 1, wherein said development pad is substantially fully overlapping with, partially overlapping with or laying adjacent to said reagent pad.

4. A method according to claim 1, wherein said first and said second porous material is selected from the group consisting of a nitrocellulose membrane, cellulose, a polymer, glass fibre, woven fibres, non-woven fibres and a chromatographic gel membrane.

5. A method according to claim 1, wherein said acidic compound is capable of providing a pH-value of said sample below 6.

6. A method according to claim 1, wherein said sample component is selected from the group consisting of proteins, carbohydrate, fat, cells, or other component present in said milk sample.

7. A method according to claim 1, wherein said development pad is located between said solid support and said reagent pad.

8. A method according to claim 1, wherein said first porous material is impregnated with o-phthalaldehyde or a derivative thereof and a colouring compound.

9. A method according to claim 1, wherein said sample is selected from the group consisting of milk, blood, serum, plasma, saliva, urine, sweat, ocular lens fluid, cerebral spinal fluid, ascites fluid, mucous fluid, synovial fluid, peritoneal fluid and amniotic fluid.

10. A method for the determination of an analyte in a sample, said method comprising the steps of:
   (a) applying said sample suspected of containing said analyte to a dry stick test device comprising:
   at least one reagent pad comprising a reagent capable of reacting with said analyte, a derivative of said analyte, or an indicator compound for said analyte to provide a detectable signal when in a moistened state, and
   a development pad which is located in contact with said reagent pad, said development pad comprising at least one controlling compound capable of providing a condition required for said reagent to react with said analyte to provide said detectable signal, wherein said development pad is located downstream from said reagent pad,
   wherein said reagent pad and said development pad are arranged to avoid precipitation of a sample component on a top-face of said dry stick test device and wherein said sample is applied on said top-face of said dry stick test device and said detectable signal is obtained from said top-face of said dry stick test device,
   wherein said controlling compound is an acidic compound and wherein said top-face of said dry stick test device relates to a surface where said sample initially contacts said reagent pad,
   (b) permitting said sample to migrate into said reagent pad and said developing pad and mobilising said reagent and said controlling compound, (c) permitting said reagent and said analyte, said derivative of said analyte or said indicator compound for said analyte to react and provide said detectable signal and
(d) detecting said detectable signal to determine the presence of said analyte in said sample.

11. A method according to claim 10, wherein said development pad is located between a solid support and said reagent pad.

12. A method according to claim 10, wherein said acidic compound is capable of providing a pH-value of said sample below 6.

13. A method according to claim 10, wherein said dry stick test device comprises at least 2 reagent pads.

14. A method according to claim 10, wherein said development pad is substantially fully overlapping with, partially overlapping with or laying adjacent to said reagent pad.

15. A method according to claim 10, wherein said analyte is selected from the group consisting of a protein, a fat, a carbohydrate, an antibiotic, a steroid, a vitamin and a chemical compound.

16. A method according to claim 15, wherein said chemical compound is selected from the group consisting of urea, triglyceride and ketone bodies.

17. A method according to claim 15, wherein said carbohydrate is selected from the group consisting of glucose and lactose.

18. A method according to claim 10, wherein said sample is collected from a mammal, said mammal is selected from the group consisting of herd animals, cows, camels, buffaloes, pigs, horses, deer, sheep, goats, pets, dogs, cats and humans.

19. A method according to claim 10, wherein said sample is selected from the group consisting of milk, blood, serum, plasma, saliva, urine, sweat, ocular lens fluid, cerebral spinal fluid, ascites fluid, mucous fluid, synovial fluid, peritoneal fluid and amniotic fluid.

20. A method according to claim 10, wherein said acidic compound is capable of providing a pH-value of said sample in a range of pH 1-6.

* * * * *